United States Patent [19]
Read et al.

[11] Patent Number: 5,993,804
[45] Date of Patent: *Nov. 30, 1999

[54] PHARMACEUTICALLY ACCEPTABLE FIXED-DRIED HUMAN BLOOD PLATELETS

[75] Inventors: Marjorie S. Read; Robert L. Reddick, both of Durham; Arthur P. Bode, Greenville, all of N.C.

[73] Assignees: The University of North Carolina at Chapel Hill, Chapel Hill; East Caroline University, Greenville, both of N.C.

[ * ] Notice: This patent is subject to a terminal disclaimer.

[21] Appl. No.: 08/775,413

[22] Filed: Dec. 31, 1996

Related U.S. Application Data

[63] Continuation of application No. 08/325,424, Nov. 28, 1994, Pat. No. 5,651,966, which is a continuation-in-part of application No. 07/891,277, May 29, 1992, abandoned.

[51] Int. Cl.⁶ ............................................. A61K 35/18
[52] U.S. Cl. .................... 424/93.72; 424/532; 435/2; 435/240.2; 435/240.31; 435/260; 436/501
[58] Field of Search ............................ 424/93.72, 532; 435/2, 240.2, 240.31, 260; 436/501

[56] References Cited

U.S. PATENT DOCUMENTS

| | | | |
|---|---|---|---|
| 4,145,185 | 3/1979 | Brinkhous et al. | 23/230 |
| 4,157,383 | 6/1979 | Sedlacek et al. | 424/3 |
| 4,199,954 | 4/1980 | McGill | 62/62 |
| 4,287,087 | 9/1981 | Brinkhous et al. | 252/408 |
| 4,302,355 | 11/1981 | Turner, Jr. et al. | 252/408 |
| 4,510,126 | 4/1985 | Fuhge et al. | 424/3 |
| 4,605,413 | 8/1986 | Urry et al. | 623/11 |
| 4,695,460 | 9/1987 | Holme | 424/101 |
| 4,717,654 | 1/1988 | Savoca et al. | 435/7 |
| 4,764,463 | 8/1988 | Mason et al. | 424/101 |
| 4,880,788 | 11/1989 | Moake et al. | 514/150 |
| 4,994,367 | 2/1991 | Bode et al. | 435/2 |
| 5,030,560 | 7/1991 | Sinor et al. | 435/7.21 |
| 5,043,261 | 8/1991 | Goodrich et al. | 435/2 |
| 5,059,518 | 10/1991 | Kortright et al. | 435/6 |
| 5,151,360 | 9/1992 | Handa et al. | 435/240.2 |
| 5,162,430 | 11/1992 | Rhee et al. | 524/54.1 |
| 5,165,938 | 11/1992 | Knighton | 424/532 |
| 5,213,814 | 5/1993 | Goodrich, Jr. et al. | 424/532 |
| 5,236,716 | 8/1993 | Carmen et al. | 424/532 |
| 5,248,506 | 9/1993 | Holme et al. | 424/533 |
| 5,344,752 | 9/1994 | Murphy | 435/2 |
| 5,358,844 | 10/1994 | Stessel et al. | 435/2 |
| 5,376,524 | 12/1994 | Murphy et al. | 435/2 |
| 5,378,601 | 1/1995 | Gepner-Puszkin | 435/2 |
| 5,651,966 | 7/1997 | Read et al. | 424/93.72 |

FOREIGN PATENT DOCUMENTS

| | | | |
|---|---|---|---|
| WO91/17655 | 11/1991 | WIPO | A01N 1/02 |

OTHER PUBLICATIONS

Keyharin, J. Cell Sci., vol. 46, pp. 289–297, 1980.
Brinkhous et al., Thromb. Res., vol. 13, pp. 591–597, 1978.
J. P. Allain et al., Platelets Fixed with Paraformaldehyde: A New Reagent for Assay of Von Willenbrand Factor and Platelet Aggregating Factor, *The Journal of Laboratory and Clinical Medicine*, 85(2), pp. 318–328, Feb. 1975.
M. Terasaki et al., Localization of Endoplasmic Reticulum in Living and Glutaraldehyde–Fixed Cells with Fluorescent Dyes, *Cell*, 38, pp. 101–108, 1984.
East Carolina University, Evaluation of Dried Storage of Platelets and RBC for Transfusion: Lyophilization and other Dehydration Techniques, *First Year Quarterly Report*, 1989.
M. S. Read et al., Rehydrated Platelets Maintain Hemostatic Properties, *The FASEB Journal Abstracts Part II*, vol. 4(1), issued Feb. 29, 1990.
Office of Naval Research, Evaluation of Dried Storage of Platelets and RBC for Transfusion: Lyophilization and other Dehydration Techniques, *First Annual Report*, 1990.
East CaroLina University, Evaluation of Dried Storage of Platelets and RBC for Transfusion: Lyophilization and other Dehydration Techniques, *Quarterly Report* (*Second Quarter, 2nd Year*), 1990.
ISTB & AABB 1990 Joint Congress, Stabilization of Platelet Membranes for Lyophilization and Dried Storage, *Book of Abstracts*, S551, 1990.
A. P. Bode et al., Stabilization of Platelet Membranes for Lyophilization and Dried Storage, *American Association of Blood Banks Congress*, 1990.
East Carolina University, Evaluation of Dried Storage of Platelets and RBC for Transfusion: Lyophilization and other Dehydration Techniques, *Quarterly Report* (*Third Quarter, 2nd Year*), 1990.
Office of Naval Research, Evaluation of Dried Storage of Platelets and RBC for Transfusion: Lyophilization and other Dehydration Techniques, *Second Annual Report*, issued Mar. 25, 1991, pp. 1–22.
M.S. Read et al., Studies with Dried and Rehydrated Platelets for Transfusion Products, *The FASEB Journal I*, vol. 5(1), issued Mar. 11, 1991.

(List continued on next page.)

*Primary Examiner*—Chhaya D. Sayala
*Attorney, Agent, or Firm*—Myers Bigel Sibley & Sajovec

[57] ABSTRACT

Fixed-dried human blood platelets and processes for preparing the same are disclosed. The platelets, upon reconstitution: adhere to thrombogenic surfaces; do not adhere to non-thrombogenic surfaces; undergo shape change (spreading) upon adhering to a thrombogenic surface; adhere to one another to form a hemostatic plug upon adhering to a thrombogenic surface; and release their granular contents. Pharmaceutical formulations containing the same are also disclosed. The platelets are preferably fixed by means of a fixative such as formaldehyde, paraformaldehyde, or glutaraldehyde, or fixed by means of a permanganate fixate. The platelets are preferably dried by lyophilization.

6 Claims, 1 Drawing Sheet

OTHER PUBLICATIONS

L. M. Graham et al., Growth Factor Production Following Prosthetic Graft Implantation, *Journal of Vascular Surgery,* 13(5), pp. 742–744, May 1991.

S. L. Goodman et al., The Effects of Substrate–Absorbed Albumin on Platelet Spreading, *J. Biomater, Sci. Polymer Edn.,* vol. 2, pp. 147–159, 1991.

A. P. Bode, Evaluation of Dried Storage of Platelets and RBC for Transfusion: Lyophilization and other Dehydration Techniques, *Quarterly Report* (*First Quarter, 3rd Year*), 1991.

A. P. Bode, Evaluation of Dried Storage of Platelets and RBC for Transfusion: Lyophilization and other Dehydration Techniques, *Quarterly Report* (*Second and Third Quarter, 3rd Year*), 1991.

Office of Naval Research, Evaluation of Dried Storage of Platelets and RBC for Transfusion: Lyophilization and other Dehydration Techniques, *Third Annual Report,* issued Apr. 21, 1992, pp. 1–11.

A. P. Bode, Evaluation of Dried Storage of Platelets and RBC for Transfusion: Lyophilization and other Dehydration Techniques, *Quarterly Report* (*Fourth Quarter, 3rd Year*), 1992.

R. P. Goodrich et al., Preservation of metabolic activity in lyophilized human erythrocytes, *Proc. Natl. Acad. Sci.,* vol. 89, pp. 967–971, 1992.

PHARMACEUTICALLY ACCEPTABLE FIXED-DRIED HUMAN BLOOD PLATELETS

This application is a continuation of application Ser. No. 08/325,424, filed Nov. 28, 1994, now U.S. Pat. No. 5,651,966 which is a Continuation-in-Part application of Ser. No. 07/891,277, filed May 29, 1992, abandoned.

This invention was made with government support under Grant No. 5-42104 awarded by the Office of Naval Research. The government has certain rights in the invention.

FIELD OF THE INVENTION

The present invention relates to fixed-dried blood platelets suitable for administration to human patients and methods of treating wound tissue by the topical application of fixed-dried platelets.

BACKGROUND OF THE INVENTION

The use of platelet concentrates in transfusion medicine has become well established during the past thirty years. However, the rapid loss of platelet function during the storage period and risk of bacterial contamination has greatly complicated management of an effective inventory of platelet concentrates in blood banks. In many settings, the limited shelf life of platelet concentrates has drastically reduced their usage.

E. Klein et al., *J. Pediatrics* 49, 517–522 (1956), describe the preparation and administration of lyophilized platelet material to children with acute leukemia and aplastic anemia. Pain and venospasm at the site of infusion were noted. The limited effectiveness of these materials is shown in Table 2 therein. After more than thirty years, these materials have not led to a useful therapeutic treatment.

In order to make platelet transfusion therapy more manageable for blood banks, there has been considerable interest in devising means for diminishing or delaying the loss of platelet function during the storage period. One approach has been in the context of the development of plasma-free storage media. See, e.g., S. Holme, U.S. Pat. No. 4,695,460. Another approach has been to employ biochemical techniques to stabilize the platelets. See, e.g., A. Bode et al., U.S. Pat. No. 4,994,367. While these techniques provide useful extension of shelf life, they do not provide a shelf life extended for prolonged periods of time. Finally, the preparation of platelet membrane microvesicles from, among other things, outdated platelets is described in F. Chao, U.S. Pat. No. 5,185,160.

Fixed-dried blood platelets for use in diagnostic assays are disclosed in U.S. Pat. No. 4,287,087 to Brinkhous et al. While such fixed-dried platelet preparations can be stored for prolonged periods of time for diagnostic purposes, they have not heretofore been provided in a form for human pharmaceutical use. Accordingly, there is a continuing need for new means of preparing blood platelet preparations having prolonged shelf lives which are suitable for administration to human patients.

SUMMARY OF THE INVENTION

A first aspect of the present invention is fixed-dried human blood platelets which, upon reconstitution: (a) adhere to thrombogenic surfaces; (b) do not adhere to non-thrombogenic surfaces; (c) undergo shape change (spreading) upon adhering to a thrombogenic surface; (d) adhere to one another to form a hemostatic plug upon adhering to a thrombogenic surface; and (e) release their granular contents, such as after stimulation and/or spreading (e.g., after receiving a physiological stimulation which would ordinarily cause a metabolically active, live or fresh platelet to release its granular contents, such as contacting wounded tissue).

A second aspect of the present invention is a pharmaceutical formulation comprised of a fixed-dried blood platelets preparation. The fixed-dried blood platelet preparation comprises fixed-dried human blood platelets having the characteristics set forth above.

A third aspect of the present invention is a method of fixing blood platelets to produce fixed-dried blood platelets having the characteristics set forth above, and the platelets so produced. The method comprises contacting the platelets to a fixative such as formaldehyde, paraformaldehyde, glutaraldehyde, or permanganate (e.g., by mixing the platelets with a solution thereof) for a time sufficient to fix or stabilize the platelets but insufficient to cause loss of the characteristics enumerated above. The platelets are then dried to yield fixed-dried blood platelets having the characteristics set forth above.

DETAILED DESCRIPTION OF THE INVENTION

Figure 1:
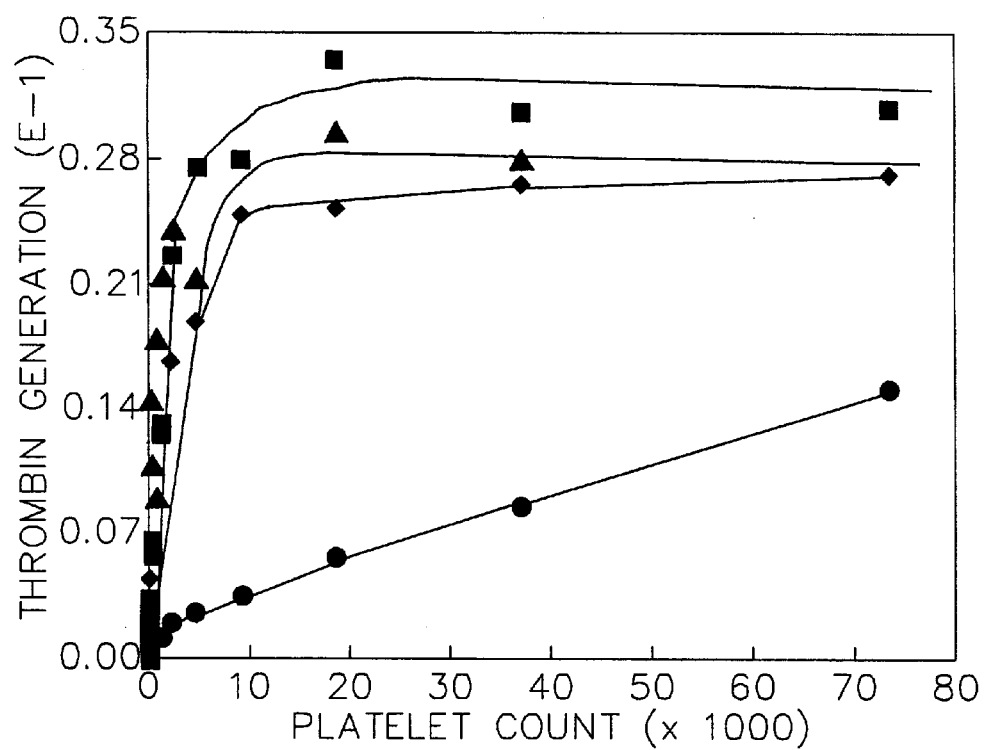
FIG. 1 shows thrombin generation by platelets of the present invention as compared to fixed-dried platelets of the prior art and unactivated control platelets.

Fixed-dried blood platelets of the present invention may be fixed with a compound selected from the group consisting of formaldehyde, paraformaldehyde and glutaraldehyde. Fixation with such agents requires careful modification of the procedure set forth in U.S. Pat. No. 4,287,087 to avoid loss of viability of the platelets. In general, washed platelets are fixed by incubating them, typically at room temperature, for up to 60 minutes in a solution of up to 1.8% paraformaldehyde. As discussed in greater detail below, care must also be taken to sufficiently fix the platelets or undue lysis will occur during drying thereof.

An alternative technique is to fix platelets by incubating the platelets in a permanganate solution (e.g., sodium permanganate, potassium permanganate). In general, washed platelets may be prepared by this technique by incubating them for from 5 to 20 minutes in from 0.001 to 1 g/dL of $KMnO_4$ or $NaMnO_4$ solution, more preferably by incubating them for from 5 to 15 minutes in from 0.005 to 0.5 g/dL of $KMnO_4$ or $NaMnO_4$ solution, and most preferably by incubating them for 8 to 12 minutes in from 0.005 to 0.05 g/dL of $KMnO_4$ or $NaMnO_4$ solution.

Blood platelet preparations for use in preparing pharmaceutical formulations should be essentially free of extraneous matter, particularly lysed blood platelets which would present free thrombogenic agents to a patient administered the preparation. Hence, care must be taken to sufficiently fix the platelets (without destroying the viability thereof, as indicated by the characteristics set forth above) prior to drying, as undue lysis will otherwise occur during the drying step. For example, platelet preparations suitable for use in preparing human pharmaceutical formulations preferably show, on reconstitution of $10^9$ platelets in one milliliter of solution, less than $10 \times 10^6$ microparticles (the fragmentary remains of lysed platelets) per milliliter, and preferably show less than 150 International Units (IU) per liter of lactate dehydrogenase in the supernatant after resuspension and pelleting (where 2200 IU per liter represents total lysis of $10^9$ cells in 1 milliliter).

Drying of platelets after fixation may be carried out by any suitable means, but is preferably carried out by lyophilization. Care must be taken to stabilize the platelet preparation prior to drying as an unacceptable level of platelet lysis may otherwise occur. Stabilization may be carried out by suspending the platelets in a solution containing a suitable water replacing molecule (or "stabilizer"), such as albumin or trehalose, and then drying the solution. In one embodiment, from 0.1 to 20 percent by weight albumin is employed, more preferably from 1 to 10 percent by weight albumin is employed, and most preferably from 5 to 10 percent by weight albumin is employed. For administration to a subject, the albumin in the preparation should be of the same species as the subject (e.g., human albumin). In the alternative, the preparation may be dried with albumin of a different species, the albumin separated from the platelets on reconstitution, and albumin of the same species added back to the reconstituted preparation for administration to the subject, but care should be taken to remove all non-species specific albumin as it may be antigenic in the subject being treated.

Pharmaceutical formulations of the present invention may simply comprise dried (preferably lyophilized) platelets, pyrogen-free and sterile in a sterile aseptic package. Albumin may be included, as noted above. Pharmaceutical formulations may also comprise a platelet preparation of the present invention reconstituted in a pharmaceutically acceptable carrier. Any aqueous carrier which rehydrates the platelets so that they possess the characteristics enumerated above and are suitable for intravenous injection may be used (e.g., sterile, pyrogen free, physiological saline solution). Additional agents, such as buffers, preservatives, and other therapeutically active agents, may also be included in the reconstituted formulation. See, e.g., U.S. Pat. No. 4,994,367 (the disclosure of which is incorporated herein by reference).

Reconstituted pharmaceutical formulations of the present invention are typically administered to human patients by intravenous injection. Patients in need of such treatment include patients afflicted with thrombocytopenia (including washout thrombocytopenia), patients afflicted with hemorrhagic platelet dysfunction, and trauma victims experiencing severe bleeding. The amount of the pharmaceutical formulation administered will vary depending upon the weight and condition of the patient, but will typically range from 20 to 350 milliliters in volume, and from $1\times10^9$ to $3\times10^9$ platelets per milliliter (and more preferably from $2\times10^9$ to $3\times10^9$ platelets per milliliter) in concentration. Pharmaceutical formulations may be packaged in a sterile, pyrogen free container to provide these volumes and dosages as a unit dose.

Also disclosed herein is a method of enhancing wound healing in a subject in need of such treatment. The method comprises topically applying fixed, dried blood platelets to the wound in an amount effective to enhance wound healing, wherein said platelets express platelet-derived growth factor on the surface thereof. The subject may be a human subject or an animal subject in veterinary medicine (i.e., dog, cat, horse, cow, etc.). The platelets may be of any suitable species (i.e., human, cow, pig, etc.) but are preferably of the same species of origin as the subject undergoing treatment. The platelets may be prepared by any suitable means so long as they express PDGF, but are preferably prepared by means such as the methods described herein so that they release platelet-derived growth factor after stimulation and/or spreading (e.g., after receiving a physiological stimulation which would ordinarily cause a metaabolically active, live or fresh platelet to release its granular contents, such as contacting wounded tissue). Any type of wound may be treated by the method, including abrasions, incisions, punctures, lacerations, burns, etc. The wound may be a wound to skin tissue, or may be a wound to the tissue of another organ, such as incisions in internal organs such as intestine, spleen, liver, etc., as encountered during surgery. The platelets may be applied to the wound by any suitable means, such as by sprinkling or spraying the platelets onto the wound, or may be applied by means of a surgical aid as discussed below. Where the platelets are sprinkled directly onto the wound, the wound may optionally then be sprayed with a clear polymeric adhesive material, or then covered with any other suitable bandage or dressing. The dosage of platelets should be at least 0.5 to $1\times10^9$ platelets per one square-centimeter of surgical aid surface area or wound surface area. The upper limit of dosage is not particularly critical, but will generally be 5 to $10\times10^9$ platelets per one square centimeter of surgical aid surface area or wound surface area.

Fixed, dried blood platelets may be applied to a wound by means of a surgical aid, such as a wound dressing or bandage, a suture, a fabric, a prosthetic device, etc. All such aids comprise, in combination, a solid, physiologically acceptable substrate material, and fixed, dried blood platelets carried by (e.g., applied as a coating to or impregnated in) the substrate material, wherein the platelets express platelet-derived growth factor on the surface thereof. Typically, such surgical aids are provided in sterile form packaged in a sterile container. The surgical aid substrate may be coated with the platelets prior to packaging (i.e., by sprinkling dried platelets onto the substrate or drying (e.g., lyophilizing) the substrate in an aqueous preparation of the fixed platelets or with an aqueous preparation of the fixed platelets carried thereon so that some of the platelets adhere to the substrate), packaged with the platelets so that some of the platelets adhere to the substrate in the package, adhered to the substrate with a suitable adhesive material, or simply sprinkled onto the surgical aid prior to application thereof to the subject.

The surgical aid substrate may take any form or be of any solid material, hydrophobic or hydrophilic, which is physiologically acceptable. Sutures, for example, can be monofilament or braided, can be biodegradable or nonbiodegradable, and can be made of materials such as nylon, silk, polyester, cotton, catgut, homopolymers and copolymers of glycolide and lactide, etc. Prosthetic devices, for example, include woven or extruded tubular structures having use in the repair of arteries, veins, ducts, asophagi; woven or knitted fabrics which are drapable or conformable and are useful surgically in hernia repair and in supporting damaged liver, kidney, and other internal organs; pins, screws, and reinforcing plates; heart valves (e.g., fixed pig heart valves), artificial tendons or cartilage material, etc. Polymeric materials as described in connection with sutures above can alternatively be cast as a thin film, sterilized, and packaged for use as a wound dressing. Bandages may be made of any suitable substrate material, such as woven or nonwoven cotton or other fabric suitable for application to or over a wound, may optionally include a backing material, and may optionally include one or more adhesive regions on the face surface thereof for securing the bandage over the wound.

The present invention is explained in greater detail in the following Examples. These Examples are for illustrative purposes only, and are not to be taken as limiting of the invention.

EXAMPLE 1

Preparation of Lyophilized Human Platelets (Protocol 1)

Human platelets are prepared from blood drawn into acid citrate dextrose (ACD) anticoagulant (0.085M trisodium citrate, 0.0702 M citric acid, 0.111 M dextrose, pH 4.5), one part anticoagulant to 5.66 parts blood. Platelets were isolated by differential centrifugation and washed three times with acid citrate saline (0.00544 M trisodium citrate, 0.154 M NaCl, adjusted to pH 6.5 with 0.1 N HCl).

After washing, platelets are fixed by incubating the washed platelets from 100 ml of blood in 5.0 ml of 1.8% paraformaldehyde solution (prepared as 9.0 ml 4% paraformaldehyde solution plus 1.0 ml ACD plus 10.0 ml 0.135 M $NaH_2PO_4$) for 45 minutes at room temperature (the fixation time may be extended to 60 minutes). An alternative is to incubate the washed platelets from 100 ml of blood in a 1.0% paraformaldehyde solution for 45 minutes at room temperature (the fixation time may be extended to 60 minutes).

To remove the paraformaldehyde, after paraformaldehyde incubation, an equal volume of imidazole buffered saline (0.084 M imidazole; 0.146 M NaCl, adjusted to pH 6.8 with 1.0 N HCl), is added to each tube and the platelets pelleted by centrifugation at 1500 times g for 8 minutes at room temperature. The supernatant is decanted and the platelets washed by resuspending the platelet pellets in 5–10 ml imidazole buffered saline pH 7.35. The wash is repeated twice more to remove the paraformaldehyde. Following the third wash the platelets are resuspended in a 5% solution of serum albumin (5 gm albumin per 100 ml of citrate saline solution, 0.0054 M sodium citrate, 0.154 M NaCl, pH 6.5). The platelets are counted using a phase contrast microscope and an American Optical Bright-Line Hemocytometer. The platelet concentration is adjusted to 800,000 per cubic millimeter (cmm).

Aliquots (10 ml) of concentration-adjusted platelets in the serum albumin solution are placed in 20 ml glass vials and frozen at −70° C. The platelets are then lyophilized for 12 hours or until a cracked, white powder is evident. The platelet product can also be shell frozen in large quantities of 100 to 500 ml and lyophilized at −40° C. for four hours, after which the temperature is raised to −25° C. for the duration of the drying time. The lyophilized product is stored at −20° C. to −70° C. until use.

Lyophilized platelets are rehydrated with 0.084 M imidazole buffer (no salt added), adjusted to a pH of 7.35 with 1.0 M NaOH. After addition of imidazole buffer, the solution is allowed to sit, undisturbed for several minutes, then gently mixed by rolling or rotating the vial to produce an even suspension of rehydrated single platelets.

EXAMPLE 2

Preparation of Lyophilized Human Platelets (Protocol 2)

Whole blood is obtained from healthy volunteer donors into commercial blood collection packs (Fenwal 4R6402, Baxter Health Care) containing its standard complement of anticoagulant (CPDA-1). The final volume of each unit of citrated whole blood collected is 500 cc. Each bag of whole blood is centrifuged to obtain platelet-rich plasma (PRP), which is aspirated from the bag and washed by three centrifugation/resuspension steps in phosphate-buffered saline solution (same as described in Example 1 above). The washed platelets are then centrifuged again and the pellet treated with a buffered solution containing 1.8% paraformaldehyde (same as described in Example 1 above) for from 45 minutes to 1 hour at room temperature. The yield of platelets after removal of the stabilization reagent and further platelet washing to remove paraformaldehyde is 60–80% of the count in the platelet suspension prior to stabilization. When albumin is not included in the washing buffer after stabilization, then the platelet yield falls.

The composition of the final platelet resuspension before freeze-drying is important to obtaining appropriate yields. In general, an effective amount of a stabilizer such as albumin or trehalose in buffered saline is necessary to obtain yields of 85–100% of the platelets through the lyophilization/rehydration steps. Albumin should be included in an amount ranging from 0.1 to 50 g/dL, more preferably an amount ranging from 1 to 25 g/dL, and most preferably in an amount ranging from 5–10 g/dL. Trehalose should be included in an amount ranging from 0.1–10. M, more preferably from 0.2 to 5 M, and most preferably from 0.5–1.0 M. Several types of rehydration solutions have been employed without noticeable differences in parameter outcomes: phosphate-buffered saline pH=7.3, tris-buffered saline pH=7.4, imidazole-buffered saline, or UNISOL™ physiologic balanced salt solution.

Typical data for rehydrated platelet preparations prepared as described in this Example are given in Table 1 below.

TABLE 1

Performance of Rehydrated Platelets in vitro

| Aggregation Studies | Percent Platelets Remaining Unaggregated |
|---|---|
| 1.5 mg/mL ristocetin | 12–15% (strong response) |
| 10 µM ADP | 42–85% (weak response) |
| 8 µg/mL collagen | 25–60% (medium response) |

| Flow Cytometry Studies | Percents Platelets with Normal Fluorescence |
|---|---|
| GPIb (AN-51, SZ-2, SZ-1, MoAbs | 90–97% (Equivalent to fresh platelets) |
| GPIIbIIIa (10E5 MoAb) | 98–99% (Equivalent to fresh platelets) |

The microparticle count after rehydration of platelet preparations prepared as described herein was from 4.5 to $5.0 \times 10^6$/mL. The hypotonic shock test response for platelets prepared as described in this Example was 0.030–0.036 OD/min (0.100–0.150 for fresh platelets). Released lactate dehydrogenase (LDH), the amount of LDH in the supernatant after resuspension of $10^9$ platelets in 1 ml of solution, was from 50 to 200 IU/L (>150 or 250 indicates significant cytoplasmic leakage).

EXAMPLE 3

Preparation of Lyophilized Human Platelets With Permanganate Stabilization

Whole blood is obtained from healthy donors into commercial blood collection packs (Fenwal 4R6402, Baxter HealthCare) containing the standard complement of anticoagulant (CPDA-1). The final volume of each unit of citrated whole blood collected is 500 cc. Each bag of whole blood is centrifuged to obtain platelet rich plasma, (PRP) which was aspirated from the bag and washed by three centrifugation/resuspension steps in a phosphate-buffered saline solution as given in Example 1 above. The washed platelets were resuspended in one-tenth volume buffered saline and added dropwise to permanganate solution comprising a phosphate-buffered saline solution containing $KMnO_4$ or $NaMnO_4$ at a final concentration of 0.01 g/dL. The suspension of platelets were incubated in the permanganate solution for 10 minutes at room temperature, and then washed twice as above with 0.1–5.0 g/dL albumin in the buffer to remove the permanganate. The loss of platelets during permanganate treatment and subsequent washing was only 10 to 20%.

To maintain yields of 70–100% after lyophilization/rehydration, it is necessary to include in the final resuspension solution prior to lyophilization a stabilizer such as trehalose or albumin, preferably in the ranges given above. Rehydration solution composition is not critical but should be isotonic and buffered to pH 7.3–7.4 (same as for paraformaldehyde-fixed platelets). Typical data upon analysis of rehydrated permanganate-fixed platelets are presented in Table 2 below.

TABLE 2

Performance of Rehydrated Platelets in vitro.

| Aggregation Studies | Percent Platelets Remaining Unaggregated |
|---|---|
| 1.5 mg/mL ristocetin | 15–32% (strong response) |
| 10 µM ADP | 27–42% (medium response) |
| 8 µg/mL collagen | 27–50% (medium response) |

| Flow Cytometry Studies | Percent Platelets with Normal Fluorescence |
|---|---|
| GPIb (AN-51, SZ-2, SZ-1, MoAbs) | 91–99% (Equivalent to fresh platelets) |
| GPIIbIIIa (10E5 MoAb) | 95–99% (Equivalent to fresh platelets) |

Microparticle count after rehydration of platelet preparations fixed by the permanganate process described in this example was $2.6$–$4.0 \times 10^6$/mL. The hypotonic shock test response for platelets prepared by this process was 0–0.030 OD/min (0.100–0.150 for fresh platelets). Released LDH was 50–200 IU/L.

EXAMPLE 4 (COMPARATIVE EXAMPLE A)

Use of Activation Markers to Characterize Paraformaldehyde Stabilized Platelets The purpose of this Example is to demonstrate that platelets fixed with paraformaldehyde in accordance with the present invention release their granular contents after contacting a thrombogenic surface, while prior art platelets do not. The platelet preparations examined were stabilized with 1.0% paraformaldehyde for 60 minutes (paraform. 1) and with 1.8% paraformaldehyde for 60 minutes (paraform. 2); these were compared to platelets prepared as described in the Brinkhous et al. patent, i.e., fixed with 2% paraformaldehyde for 120 minutes (Brinkhous).

The markers employed in the tests described in Table 3, CD62 and GP53, are commercially available antibodies purchased from Becton-Dickinson, Inc. and are used to indicate the presence on the surface of the platelet of antigens released from platelet granules. The presence of granule-released antigens on a platelet surface is taken as evidence of platelet activation. Antibodies against these antigens are referred to as activation markers. Antibodies against Platelet-derived growth factor (PDGF) are used to detect platelet membrane bound PDGF. The PDGF antibody was purchased from Genzyme (Cambridge, Mass.). The vessels used in the Baumgartner adhesiveness tests were obtained from a normal dog.

Experiments were carried out to demonstrate the activatability of separate lyophilized platelet preparations by incorporating them into fresh whole blood made free of native platelets by differential centrifugation for comparison to fresh, unsubstituted whole blood for use in annular perfusion chambers. Blood was collected into citrate anticoagulant (CPDA-1) from normal human donors. Two 1 cm strips of canine arterial vessel were everted on a tapered rod and inserted into a recirculation loop driven by a peristaltic pump at 130 mL/minute. The loop was perfused first with buffer, then the blood (with either fresh or lyophilized platelets) for 5 minutes at room temperature, followed by a 2 minute perfusion with 2% paraformaldehyde to fix adherent platelets to the vessel permanently. Platelets on the vessel surface were detected by additional of a fluorescent monoclonal antibody to GPIIbIIIa. Adherence was quantified by epi-fluorescence microscopy as an estimate of the percent of vessel surface covered by fluorescent cells. Also, the remaining blood (with non-adherent platelets) was sampled to make platelet-rich plasma (PRP). The PRP was further fixed with 2% paraformaldehyde for 1–2 hours at room temperature before incubation with florescence-labelled monoclonal antibodies to CD62 or GP53 or PDGF. The presence of these markers on the surface of platelets in the sample was detected by standard flow cytometry on a Becton Dickinson FACSCAN™ flow cytometer. Quantitation of results was expressed as the percentage of platelets with fluorescence greater than the background recorded with a non-specific control antibody (non-immune mouse $IgG2_8$). The findings were compared on blood samples taken just prior to or just after initiation of perfusion of the vessel strips. The results of this comparison are shown in Table 3.

TABLE 3

Comparison of Paraformaldehyde Stabilized Platelets with Activation Markers.

| | Percent Positive Platelets | |
|---|---|---|
| Marker | Pre-Circulation | Post-Circulation |
| 1.0% Paraformaldehyde/60 minutes (Paraform. 1) | | |
| CD62 | 12 | 16 |
| GP53 | 18 | 22 |
| PDGF | 20 | 24 |
| 1.8% Paraformaldehyde/60 minutes (Paraform. 2) | | |
| CD62 | 6, 3 | 12, 7 |
| GP53 | 14, 19 | 21, 30 |
| PDGF | 12, 18 | 18, 40 |
| 2.0% Paraformaldehyde/120 minutes (Brinkhous) | | |
| CD62 | 11 | 6 |
| GP53 | 1 | 1 |
| PDGF | 27 | 30 |

From Table 3, it can be seen that the concentration and time of stabilization results in platelets with substantially different properties. Paraform. 1 and paraform. 2 platelets showed an increasing number of activation markers present on platelets in blood circulated across the subendothelial surface of the vessel wall. Paraform. 2 shows a doubling of the activation markers following exposure to an activating surface. In contrast, the Brinkhous preparation shows essentially no activation post circulation with the CD62 marker and minimal change in PDGF.

EXAMPLE 5 (COMPARATIVE EXAMPLE B)

Use of Activation Markers to Characterize Platelets Prepared with Potassium Permanganate The purpose of this Example is to demonstrate that platelets fixed with permanganate in accordance with the present invention release their granular contents after contacting a thrombogenic surface, while prior art platelets do not. This example was carried out in essentially the same manner as Example 4 above, except with platelets fixed with permanganate as described in Example 3 above. Three different permanganate-fixed platelet preparations were employed: platelets stabilized with 0.02 M permanganate and lyophilized in the presence of Trehalose (Perm. 1); platelets stabilized with 0.02 M permanganate and lyophilized in the presence of human serum albumin (Perm. 2); and platelets stabilized with 0.01 M permanganate and lyophilized in the presence of human serum albumin (Perm. 3). For comparative purposes, platelets were also fixed with 2% paraformaldehyde for 120 minutes and dried in the presence of bovine serum albumin. Data are given in Table 4 below.

From Table 4 it can be seen that, in contrast to permanganate-fixed platelets of the present invention, the Brinkhous platelet preparation showed essentially no activation following exposure to a thrombogenic vessel.

TABLE 4

Comparison of Permanganate Sabilized Platelets with Activation Markers.

| | CD62 Marker (% Positive Platelets) | |
|---|---|---|
| Platelets | Pre-Circulation | Post-Circulation |
| Perm. 1 | 39 | 86 |
| Perm. 2 | 31 | 60 |
| Perm. 3 | ND | 37 |
| Brinkhous | 11 | 6 |

EXAMPLE 6 (COMPARATIVE EXAMPLE C)

Adherence of Rehydrated Platelets to Vessel Subendothelium

The ability of fresh and rehydrated platelets to adhere to exposed subendothelial vessel wall was tested in an annular perfusion chamber. the Brinkhous platelet preparation and platelets prepared as described in Examples 4 and 5 above, were compared. Platelets were removed from ACD anticoagulated whole blood and replaced with various preparations of dried and rehydrated platelets. Whole blood and blood containing rehydrated platelets was then pumped through chambers containing several everted vessels. The flow and shear rates were constant for all preparations. Results are shown in Table 5 below.

TABLE 5

Adherence of Rehydrated Platelets to Vessel Subendothelium.

| Platelet Type | Percent Coverage |
|---|---|
| Fresh | 53–76 |
| Perm. 2 | 26–53 |
| Paraform. 2 | 23–43 |
| Brinkhous | 44–80 |

Although variability was high between runs, it is evident that the Brinkhous platelets were "sticker" than the other preparations. All preparations adhere to vessel subendothelium but less area of the exposed vessel wall is covered by platelets prepared by the present invention. Of course, adherence of the prior art platelets, which are metabolically "dead," is a passive property which would not be followed by an appropriate metabolic response.

EXAMPLE 7 (COMPARATIVE EXAMPLE D)

Hypotonic Shock Recovery Test

The hypotonic shock recovery test is used to assess the ability of platelets to remove water and recover from swelling caused by increased water uptake by the platelet. To measure the extent of recovery from swelling, platelet suspensions at $3 \times 10^8$/mL in citrated plasma were treated with ½ volume deionized water in a Chronolog aggregometer at 37° C. The light transmittance signal (% T) increases immediately with the uptake of water by platelets due to hypotonic shock (% $T_{max}$), followed by a return of % T to near baseline (% $T_{base}$, corrected for dilution) as the water is actively expelled by intact platelets. The extent of recovery after 10 minutes was quantified as:

$$\frac{(\%T_{max} - \%T_{actual})}{(\%T_{max} - \%T_{base})} \times 100$$

The rate of recovery from hypotonic shock was a separate measurement, carried out as above except at 22° C. in an unstirred Payton aggregometer. The rate of recovery was computed as the rate of change in % T from 1 minute to 3 minutes after addition of deionized water. The results given in Table 6 are expressed as a percentage of the rate of change in % T obtained with fresh platelet controls. The rate and extent of recovery of platelets in hypotonic shock tests depends largely on membrane integrity and residual metabolic activity. The Brinkhous platelet preparations were non-responsive; while platelet preparations of the present invention showed 40 to 100% recovery.

TABLE 6

Hypotonic Shock Recovery of Different Stabilized Platelet Preparations.

| Platelet Preparation | Recovery | |
|---|---|---|
| | Rate | Extent |
| Perm. 1 | 0–10 | 40 |
| Perm. 2 | 0–8 | — |
| Paraform. 2 | 26–43 | 100 |
| Brinkhous | 0 | 0 |

EXAMPLE 8 (COMPARATIVE EXAMPLE E)

Thrombin Generation by Platelet Preparations

The purpose of this Example is to illustrate that small changes in concentration of fixative and time of fixation result in a different response of platelets to stimuli.

Four platelet preparations were tested for thrombin generation (which is platelet concentration dependent) and support of the prothrombinase complex on the surface of the platelets. Results are shown in FIG. 1. Platelet count ×1000 is given on the horizontal axis; thrombin generation in units is given on the vertical axis. The preparations were: (i) paraform. 1 platelets (triangles in FIG. 1); (ii) paraform. 2 platelets (squares); (iii) Brinkhous platelets (diamonds); and (iv) fresh, washed platelets as a control (circles). Paraform. 2 platelets showed the maximum rate of thrombin generation followed by paraform. 1 platelets, and then Brinkhous platelets. Control platelets showed the lowest rate of thrombin generation.

EXAMPLE 9

Expression of Platelet-Derived Growth Factor (PDGF) on Surface of Fixed-Dried Platelets The purpose of this Example was to examine platelets fixed and dried by various means for the expression of PDGF on the surface thereof. Antibodies and platelet preparations are as described in Examples 5 and 6 above; data is given in Table 7 below.

TABLE 7

Expression of PDGF on Platelet Surface.

| | Percent Platelets Positive for PDGF | |
|---|---|---|
| Preparation | Pre-Circulation | Post-Circulation |
| Fresh Blood | 45 | 67 |
| Perm. 2 | ND | 64 |
| Paraform. 1 | 37 | 34 |
| Paraform. 2 | 28 | 40 |
| Brinkhous | 27 | 30 |

These data indicate that both the Brinkhous platelets and platelets of the present invention express PDGF on the surface thereof, and that the Perm. 2 and Paraform. 2 platelets express more PDGF on the surface than Brinkhous platelets before or after stimulation.

EXAMPLE 10

Topical Administration of Fixed-Dried Platelets Which Express PDGF to Facilitate Wound Healing in Pig This example describes the use of platelets which express PDGF on the surface thereof to facilitate wound healing in pigs.

Porcine platelets used in this experiment were prepared essentially in the manner described in Example 1 above, modified as set forth below. To remove the paraformaldehyde, an equal volume of imidazole buffered-saline, (IBS) pH 7.35, is added. The platelets are pelleted by centrifugation at 1500 xg for 8 minutes at room temperature. The supernatant is discarded and the pellet resuspended in 5–10 ml IBS, pH 6.8. The wash was repeated twice. The procedure is then the same as described in Example 1, except the concentration of porcine platelets is $8 \times 10^4/\mu l$. Porcine albumin was added as a stabilizer for drying, in an amount similar to that described in Example 2.

The platelet dressing was prepared using BIOBRANE II™ surgical dressing on 1 square centimeter sections (Don B. Howland, Inc. Sugarland, Tex.) in 10 cm diameter petri dishes. 1 cm² of the dressing was saturated with $3.2 \times 10^9$ porcine platelets by pipetting 1 ml of solution containing the said amount of platelets on the dressing, then carefully transferring the dressing with the platelets into a lyophilization chamber, and the material dried at −40° C. until a cracked white powder was evident.

Two adult pigs were studied. The pigs were anesthetised and controlled punch wounds were made using a dermatologic 3 millimeter (mm) punch. on day 0, wounds of 3 mm deep×3 mm wide were produced in the shaved sterilized area along the back of anesthetised pigs. The wound penetrates the epidermis, dermis and fatty tissue. Three rows of 6 wounds each were produced. Row 1 was treated with dried platelets. Row 2 was treated with mesh impregnated with dried platelets. Row three was left untreated. On day 1, wound one of each row was removed. On day 2, wound 2 of each row was removed. On each day for the next 4 days each succeeding wound of each row was removed for study. The removed tissue was fixed with formaldehyde and treated with standard histologic techniques, stained and examined microscopically for evidence of wound repair. Each section was examined for presence of platelets, fibroblastic proliferation along the sides and at the bottom of the wound, epithelial regrowth and evidence of inflammatory response. The amount of platelets packed into each site was not determined exactly. Wounds in row one were filled with dried platelets. Each punch wound was filled to capacity with dried platelets. Wounds in row 2 were treated by packing 1 cm² mesh containing dried platelets into each wound.

Qualitatively, all the treated sections showed advanced repair as compared to the untreated wounds.

EXAMPLE 11

Intraveneous Administration of Fixed-Dried Platelets Normal and von Willebrand Disease Dogs To measure in vivo hemostatic effectiveness of rehydrated platelets, two normal dogs and one von Willebrand factor deficient (von Willebrand disease, vWD) dog were infused with rehydrated fixed-dried normal canine platelets. The canine platelets were fixed, dried and reconstituted in essentially the same manner as human platelets as described in Examples 1 and 2 above, except that the platelets were fixed in 0.67% paraformaldehyde solution for one hours. Table 8 below shows the physical data relative to the infusion and characteristics of the dogs.

TABLE 8

Infusion of Rehydrated Platelets (RP) into Normal (N) and von Willebrand Disease (vWD) dogs.

| | Phenotype | | |
|---|---|---|---|
| Physical Data | N | N | vWD |
| Weight (Kg) | 20 | 15.9 | 9.1 |
| Platelet Count (×10⁶) | 255 | 225 | 285 |
| Total Circulating Platelets (×10⁹) | 448 | 315 | 228 |
| RP Infused (ml) | 10 | 9.2 | 8.5 |
| Total RP (×10⁹) | 82.5 | 138 | 117 |
| Total RP (% Original Platelets) | 18.4 | 43 | 51 |
| % vWF (initial) | 100 | 100 | 0 |
| % vWF (post cryo.) | — | — | 50 |
| BT (min:sec) Initial | 2:28 | 1:55 | >15 |
| BT (min:sec) post cryo. | — | — | 7:52 |
| BT (min:sec) post cryo., post RP | 2:52 | 1:55 | 6:40 |

Following infusion of platelets into dogs, above, blood samples were collected throughout the experiment, approximately four hours, as follows. An anesthetized dog is infused with rehydrated platelets. The carotid arteries are exposed. A cannula is placed in the femoral artery for measuring blood pressure and a second cannula is placed in the femoral vein for sample collection and administration of fluids. One carotid artery is subjected to a pinch injury with added stenosis in accordance with known techniques (See Nichols et al., *Circulation Research* 59, 15–26 (1988)). The dogs are monitored for changes in blood pressure, heart rate, respiration etc. to evaluate any adverse response to infusions of fixed-dried platelets. Rehydrated platelets are labeled with a fluorescent dye, infused and blood samples collected to examine for presence of labeled rehydrated platelets in the peripheral circulation, in the formed thrombus, in areas of the disrupted vessel wall (subendothelium) and adherent to normal vessel wall. Cuts were made in the margin of the dog's ears and sections were prepared for microscopic examination for adherent rehydrated platelets. Table 9 shows the results of those studies.

TABLE 9

Effect of Infusion of Rehydrated Platelets (RP) into Normal (N) and von Willebrand Disease (vWD) dogs.

|  | Phenotype | | |
| --- | --- | --- | --- |
| Test | N | N | vWD |
| Transfusion Reaction | none | none | none |
| RP In Peripheral Circulation | yes | yes | yes |
| RP Present in Formed Thrombi | yes | yes | yes |
| RP Adhesion to Subendothelium | yes | yes | yes |
| RP Adhesion to normal vessel wall | no | no | no |
| RP Adhesion to cut surface | yes | yes | yes |

The foregoing examples are illustrative of the present invention, and are not to be construed as limiting thereof. The invention is defined by the following claims, with equivalents of the claims to be included therein.

That which is claimed is:

1. A pharmaceutical formulation comprising fixed-dried blood platelets, said fixed-dried blood platelets consisting essentially of human blood platelets which, upon reconstitution in an aqueous pharmaceutically acceptable carrier:
   adhere to thrombogenic surfaces;
   do not adhere to non-thrombogenic surfaces;
   undergo shape change upon adhering to a thrombogenic surface;
   adhere to one another to form a hemostatic plug upon adhering to a thrombogenic surface; and
   release their granular contents.

2. A pharmaceutical formulation according to claim 1, further comprising albumin.

3. A pharmaceutical formulation according to claim 1, further comprising human albumin.

4. A pharmaceutical formulation according to claim 1, wherein said platelets are dried by lyophilization.

5. A pharmaceutical formulation according to claim 1, wherein said platelets are fixed with a compound selected from the group consisting of formaldehyde, paraformaldehyde and glutaraldehyde.

6. A pharmaceutical formulation according to claim 1, wherein said platelets are fixed with permanganate.

* * * * *

UNITED STATES PATENT AND TRADEMARK OFFICE
CERTIFICATE OF CORRECTION

PATENT NO.   : 5,993,804
DATED        : November 30, 1999
INVENTOR(S)  : Read et al.

It is certified that error appears in the above-identified patent and that said Letters Patent is hereby corrected as shown below:

<u>Column 1,</u>
Line 12, please insert the following paragraph immediately prior to the heading "Field of the Invention":

-- STATEMENT OF FEDERAL SUPPORT
The present invention was made with Government support under Grant Numbers N00014-89-J-1712 and N00014-97-0891 from the Office of Naval Research. The Government has certain rights to this Invention. --

Signed and Sealed this

Twenty-first Day of January, 2003

JAMES E. ROGAN
*Director of the United States Patent and Trademark Office*